United States Patent [19]

Kerrigan

[11] Plant 5,149

[45] Nov. 29, 1983

[54] RHODODENDRON PLANT 'GOLDILOCKS'

[76] Inventor: Howard Kerrigan, 24249 Second St., Hayward, Calif. 94541

[21] Appl. No.: 360,618

[22] Filed: Mar. 22, 1982

[51] Int. Cl.[3] ..... A01H 5/00
[52] U.S. Cl. ..... Plt./55
[58] Field of Search ..... Plt./55

*Primary Examiner*—James R. Feyrer
*Attorney, Agent, or Firm*—James R. Cypher

[57] ABSTRACT

The new cultivar 'Goldilocks' was derived from a cross between unnamed plants belonging to *Rhododendron chryseum* and *R. xanthostephaanum,* and is distinguished particularly by its compact habit and profuse, uniform display of deep yellow blooms.

2 Drawing Figures

BACKGROUND OF THE INVENTION

The invention is a new and distinct variety of rhododendron plant originated by me in 1952 as a consequence of a breeding program begun in 1943.

The parentage of my new rhododendron is as follows: The seed parent was *R. chryseum,* Cultivar (unnamed), and the pollen parent was *R. xanthostephanum,* Cultivar (unnamed).

The object of the cross was to produce a compact dwarf plant with good yellow colored bloom.

These objectives were achieved along with other desirable improvements, as evidenced by the following unique combination of characteristics which are outstanding in the new variety and which distinguish it from its parents as well as from all other varieties of which I am aware.

My new variety is characterized by: compact growth with deep yellow blooms borne in profusion.

It is unlike any other rhododendron known to me. It differs from its seed parent by its taller and more rapid growth, larger leaves, and deep yellow flowers. It resembles its pollen parent only in the color of its bloom.

Asexual reproduction of my variety by cuttings through a series of annual propagations at Oakland and Hayward, Calif. shows that all characteristics of the variety come true to form through succeeding generations.

DESCRIPTION OF THE PHOTOGRAPH

This new cultivar named Goldilocks is illustrated by the accompanying photographs which show the growing habit and foliage of the plant, and the color and detailed characteristics of its bloom. Photograph 1 is a color photo of a top view of the entire plant showing the distinguishing features of the plant, and Photograph 2 is a close-up photo of the inflorescence. The photographs were taken outdoors in daylight at Hayward, Calif.

DETAILED BOTANICAL DESCRIPTION OF THE PLANT

The following botanical description is based upon observations of container grown cuttings in Oakland and Hayward, Calif. The plants were propagated in greenhouses and then grown outdoors. The color references cited are those of the horticultural color charts of The Royal Horticultural Society.

Taxonomic Status: Hybrid Cultivar.

*Genus.*—Rhododendron.

*Seed parent.*—*R. chryseum,* Cultivar (unnamed).

*Pollen parent.*—*R. xanthostephanum,* Cultivar (unnamed).

Growth habit: Slow growth, Dwarf type, with a dense, compact form developing a crown approximately 60 cm. board, about 45 cm. above the soil.

Foliage:

*Size.*—Blade 1.2 - 3.5 cm. long ×0.4 - 1.0 cm. broad.

*Petiole.*—0.5 cm. long; 0.1 cm. broad.

*Shape.*—Narrowly elliptic, with acute apex.

*Color.*—Adaxial surface, about "parsley green" 009 62/1.

*Texture.*—Adaxial surface minutely punctuate, slightly lustrous, glabrous. Leaf under surfaces contain scales.

Inflorescence:

*Arrangement.*—In terminal and subterminal clusters 3 - 6 blooms per bud, these with pedicels 0.8 - 1.0 cm. long×0.1 cm. broad.

*Calyx.*—Pentamerous, the lobes broadly lanceolate 3 - 4 mm×1.5 - 2.5 mm., color "pea green" 6½, texture minutely scabrous.

*Corolla.*—Size: Small, about 1.0 cm. long×2.0 - 2.5 cm. broad when fully open. Shape: Short funnel form. Form: Pentamerous, of a single whorl. Color: Adaxially "sap green", 62, becoming "uranium green" 63; adaxially slightly more green than "primrose yellow" 60½. Markings: A single conspicuous mid-vein, with faint lateral veins, these slightly darker than the background. Texture: Rugose, dull. Androecium: 10 or fewer stamens in two alternating ranks, 1.3 cm. and 1.0 cm. long respectively. Gynoecium: Stigma and style about 1.7 cm. long, above a 5 loculed ovary, this about 0.2 - 0.3 cm. long.

Blooming habit: It blooms out evenly over the entire plant.

Blooming season: The new cultivar usually is in peak bloom about the first of April in Hayward, Calif., and about mid-April in Canby, Oreg. (North-Western part of the state). However, blooming time will vary from year to year depending upon the weather, and in 1983 the new cultivar was in peak bloom in both Hayward, Calif. and Canby, Oreg. during mid-March.

Hardiness: The new cultivar has experienced temperatures as low as 5 degrees Fahrenheit without damage.

I claim:

1. A new and distinct variety of rhododendron plant substantially as herein shown and described primarily characterized by: Compact growth with deep yellow blooms borne in profusion.

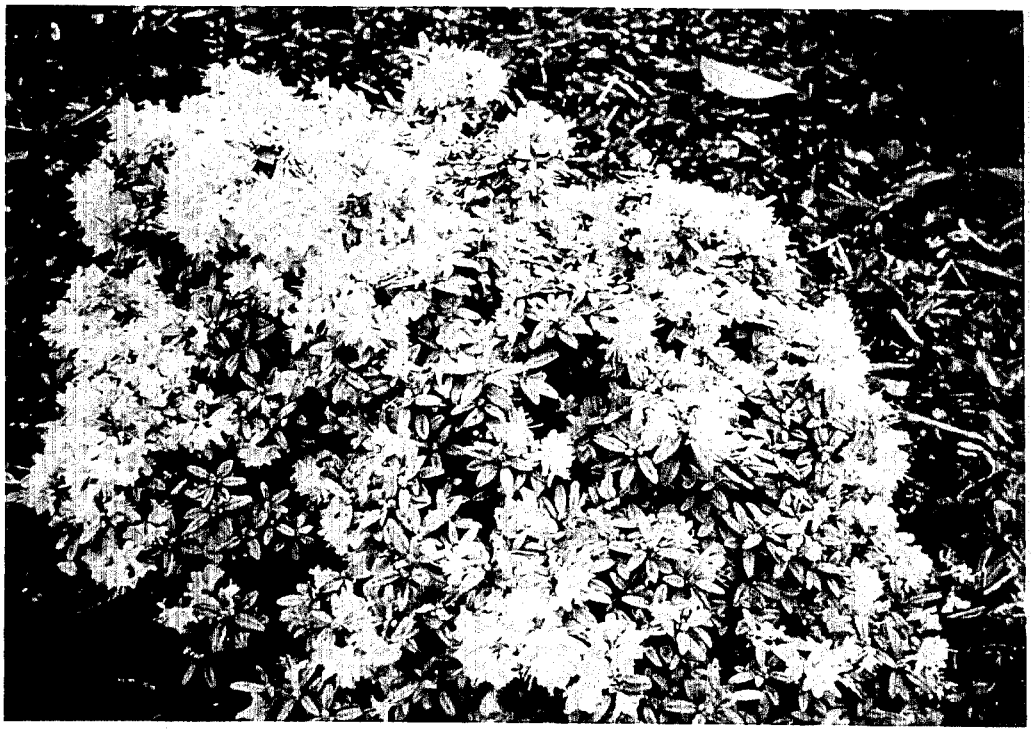

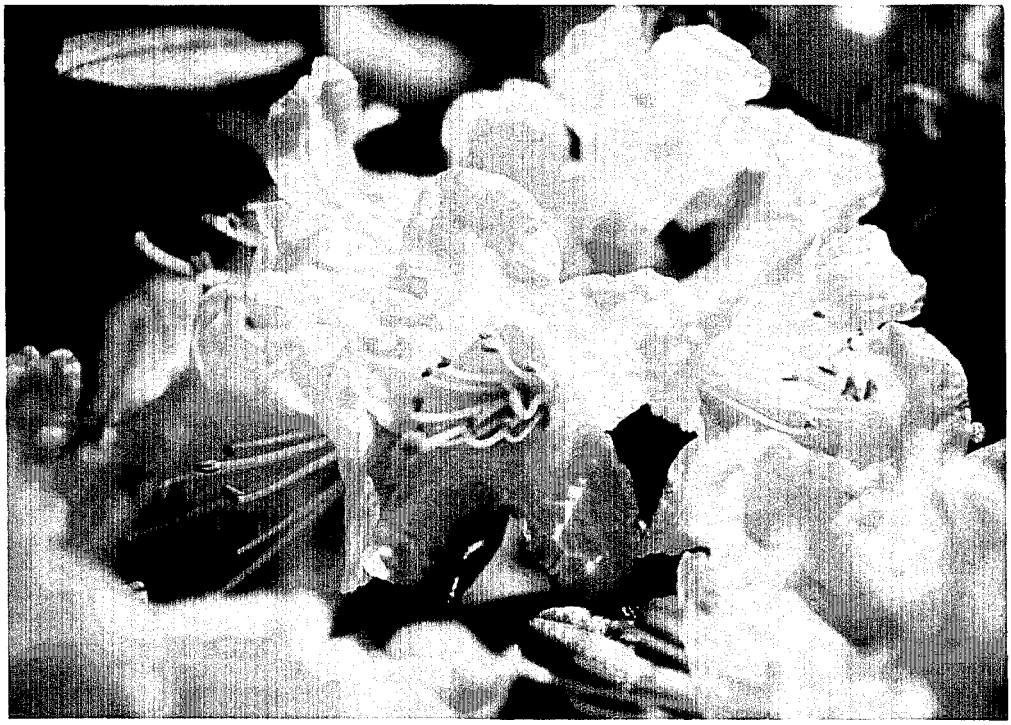

* * * * *